United States Patent [19]

Lachut

[11] Patent Number: 5,516,747

[45] Date of Patent: May 14, 1996

[54] PESTICIDAL SURFACTANT MIXTURES COMPRISING ALKYL POLYGLYCOSIDES AND ALKYL NAPHTHALENE SULFONATES

[75] Inventor: Frank J. Lachut, West Chester, Ohio

[73] Assignee: Henkel Corporation, Plymouth Meeting, Pa.

[21] Appl. No.: 229,046

[22] Filed: Apr. 18, 1994

[51] Int. Cl.$^6$ .......................... A01N 25/30; A01N 43/04
[52] U.S. Cl. .................. 504/116; 71/DIG. 1; 514/54;
514/777; 514/778; 514/975
[58] Field of Search .................................. 514/777, 778,
514/54, 975; 504/116; 71/DIG. 1

[56] References Cited

U.S. PATENT DOCUMENTS

| H303 | 7/1987 | Malik et al. ........................ 514/85 |
| 3,547,828 | 12/1970 | Mansfield et al. ................ 252/351 |
| 4,663,069 | 5/1987 | Llenado .............................. 252/117 |
| 4,888,325 | 12/1989 | Schroeder et al. ................. 514/25 |
| 5,008,277 | 4/1991 | Plummer ............................ 514/336 |
| 5,008,292 | 4/1991 | Ecsery et al. ...................... 514/654 |
| 5,104,585 | 4/1992 | Fabry et al. ........................ 252/555 |
| 5,110,981 | 5/1992 | Milstein ............................... 562/90 |
| 5,138,046 | 8/1992 | Wuest et al. ...................... 536/18.6 |
| 5,140,019 | 8/1992 | Wada et al. ......................... 514/89 |
| 5,324,708 | 6/1994 | Moreno et al. ..................... 504/206 |
| 5,385,750 | 1/1995 | Aleksejczyk et al. .............. 427/4 |

FOREIGN PATENT DOCUMENTS

| 0070074 | 1/1983 | European Pat. Off. . |
| 0092355 | 10/1983 | European Pat. Off. . |
| 0301298 | 2/1989 | European Pat. Off. . |
| 0357969 | 3/1990 | European Pat. Off. . |
| 0362671 | 4/1990 | European Pat. Off. . |

*Primary Examiner*—S. Mark Clardy
*Attorney, Agent, or Firm*—Ernest G. Szoke; Wayne C. Jaeschke; Henry E. Millson, Jr.

[57] ABSTRACT

Surfactant mixtures of an alkyl naphthalene sulfonate and an alkyl polyglycoside, wherein the alkyl polyglycoside is present in from 5 to 25% by weight of the surfactant mixture, and aqueous pesticide compositions containing the surfactant mixture.

20 Claims, 2 Drawing Sheets

PESTICIDAL SURFACTANT MIXTURES COMPRISING ALKYL POLYGLYCOSIDES AND ALKYL NAPHTHALENE SULFONATES

BACKGROUND OF THE INVENTION

1. Field of the Invention

The present invention relates to surfactant mixtures and to pesticide compositions containing them.

2. Statement of Related Art

Pesticide compositions are generally applied to agricultural crops, e.g. plants, bushes, vines, and trees by spraying the compositions in the form of dilute aqueous solutions, dispersions, or emulsions. Such compositions normally contain small quantities of environmentally acceptable wetting agents, which can serve as a dispersion or emulsifying agent for the other components of the compositions as well as a wetting agent to obtain a more uniform coating of the composition on the agricultural crops to which they are applied. Such wetting agents include synthetic surfactants such as alkyl benzene sulfonates and alkyl naphthalene sulfonates..

Detergent mixtures containing alkyl polyglycoside surfactants and certain sulfonates, such as hydroxyalkyl sulfonates and alkylbenzene sulfonates are known for use in washing textiles and for other industrial uses. See e.g. U.S. Pat. No. 5,104,585 to Fabry et al., and U.S. Pat. No. 4,663,069 and EPA 0 070 074 to Lienado.

DESCRIPTION OF THE INVENTION

Figure 1:
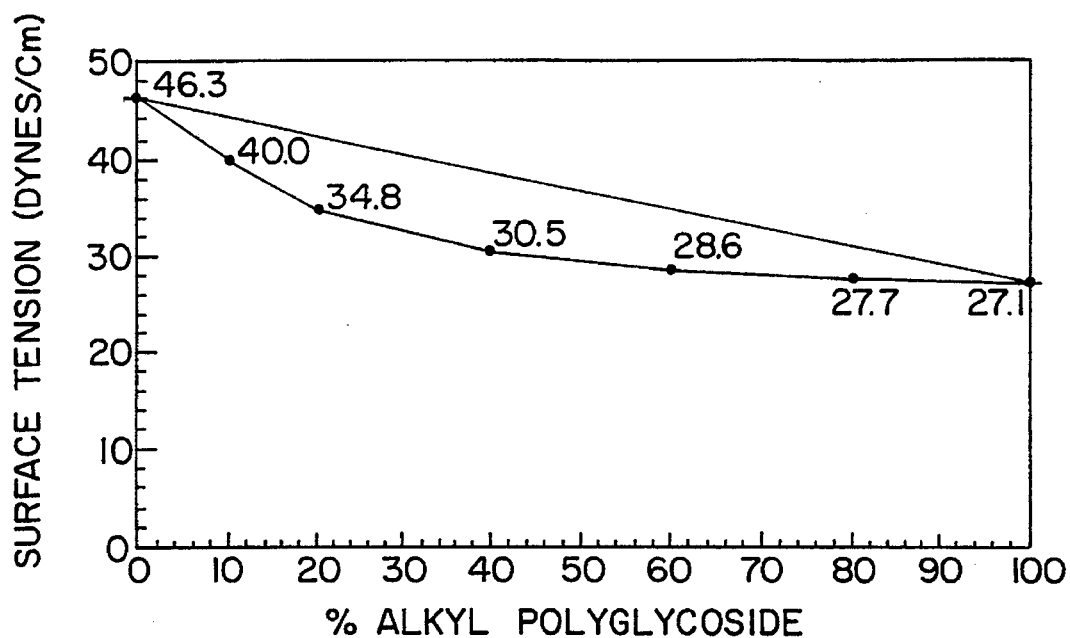
FIGS. 1–4 show the surface tensions of aqueous solutions of various mixtures of alkyl naphthalene sulfonates and alkyl polyglycosides.

Other than in the operating examples, or where otherwise indicated, all numbers expressing quantities of ingredients or reaction conditions used herein are to be understood as modified in all instances by the term "about".

It has now been discovered that the addition of relatively small quantities of alkyl polyglycosides to alkyl naphthalene sulfonates results in a marked improvement in the surface tension of aqueous solutions of the resulting mixtures, and that aqueous agricultural compositions containing one or more pesticides and the above surfactant mixtures can be applied more uniformly to agricultural crops than identical compositions without the alkyl polyglycoside.

The surfactant mixtures of the invention comprise

A) at least one alkyl naphthalene sulfonate, and

B) at least one alkyl polyglycoside, wherein component B) is present in from 5 to 25%, preferably 10 to 20% by weight, based on the combined weight of components A) and B).

The above surfactant mixtures can be formulated as concentrated aqueous solutions, e.g. containing from 50 to 94%, preferably from 50 to 75% by weight of water, which can then be diluted, e.g. to an aqueous solution ready for mixing with one or more pesticides, containing up to 99.99% by weight of water, e.g. from 95 to 99.99% by weight of water.

The alkyl naphthalene sulfonates of component A) are known compounds and include compounds of the formula

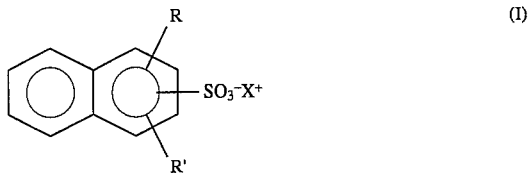

wherein R and R' are independently hydrogen, a $C_{1-30}$ straight or branched chain alkyl or alkenyl group, preferably a $C_{1-4}$ alkyl group, and provided that both R and R' cannot be hydrogen, and $x^-$ is hydrogen, an alkali metal, an alkaline earth metal, ammonium, a mono-, di-, or tri- $C_{1-4}$ alkyl ammonium, or a mono-, di-. or tri- $C_{1-4}$ hydroxyalkyl ammonium cation. In the above formula I, it is understood that the R and R' groups can be present in any position on the naphthalene nucleus.

The alkyl naphthalene sulfonates of formula I are preferably manufactured by the process of U.S. Pat. No. 5,110,981 to Milstein. As stated in this patent, the alkyl naphthalene sulfonates are usually obtained in the form of mixtures, containing both mono- and di-alkyl sulfonates, as well as small quantities of unreacted naphthalene and/or unsulfonated alkyl naphthalenes which will not interfere with their use in the practice of the present invention.

The alkyl polyglycosides of component B) are also known compounds and have the formula

wherein $R^2$ is a straight or branched chain $C_{8-22}$ alkyl or alkenyl radical, G is a glycose unit, and n is a number of from 1 to 10, preferably 1.8 or less, e.g. from 1.2 to 1.7. $R^2$ is preferably a $C_{10-18}$ straight chain alkyl group.

The above alkyl polyglycosides present in the surfactant mixtures according to the invention and their production are described, for example in European patent applications EP 92 355, EP 301 298, EP 357 969, EP 362 671 and U.S. Pat. No. 3,547,828. The glycoside components $((G)_n$ in formula II) of these alkyl glycosides are oligomers or polymers of naturally occurring aldose or ketose monomers, including in particular glucose, mannose, fructose, galactose, talose, gulose, altrose, allose, idose, ribose, arabinose, xylose and lyxose. The oligomers consisting of these glycoside-bonded monomers are characterized not only by the type of sugar present therein, but also by their number, the so called degree of oligomerization. As an analytically determined quantity, the degree of oligomerization (n in formula II) is generally a fractional number and is in the range of from 1 to 10 and, in the case of the alkyl glycosides preferably used, is in the range of from 1.2 to 1.8. Since the reaction products of sugars and alcohols are generally mixtures, the term "alkyl polyglycoside" encompasses both alkyl monoglycosides and alkyl poly (oligo) glycosides. By virtue of its ready availability, glucose is the preferred monomer unit.

The alkyl moiety ($R^2$ in formula II) of the alkyl polyglycosides present in the surfactant mixtures according to the invention also is preferably obtained from readily available derivatives of renewable raw materials, more particularly from fatty alcohols, although branched-chain primary alcohols, particularly so-called oxo alcohols, for example nonyl, undecyl or tridecyl alcohols, can also be used for the production of the above alkyl polyglycosides. Primary alcohols containing linear octyl, decyl, dodecyl, tetradecyl, hexadecyl or octadecyl groups and mixtures thereof are particularly useful. Particularly suitable alkyl glycosides contain a coconut oil fatty alkyl radical, i.e. mixtures in which essentially $R^2$=dodecyl and $R^2$= tetradecyl. Where the $R^2$ group is derived from natural fats, both saturated (alkyl) and unsaturated (alkenyl) groups are often present.

For their production, the alkyl glycosides may contain small quantities, for example 1 to 2%, of unreacted long-chain alcohol which does not adversely affect the properties of the surfactant mixtures produced with them.

The present invention also relates to aqueous pesticide compositions comprising
A) at least one alkyl naphthalene sulfonate;
B) at least one alkyl polyglycoside; and
C) at least one pesticide;
wherein component B) is present in from 5 to 25%, preferably 10 to 20% by weight, based on the combined weight of components A) and B).

Preferably, component C) is present in from 0.001 to 25%, more preferably from 0.1 to 10% by weight, based on the weight of the aqueous pesticide composition. The weight percentage of component C) will depend on various factors such as the number of pesticides present, their activities, the quantities desired on the relevant crop or crops, and the like.

The surfactant mixture of component A) plus component B) is preferably present in from 0.01 to 5% by weight, more preferably from 0.1 to 1.5% by weight, also based on the weight of the aqueous pesticide composition.

Components A) and B) are as described above. Component C) includes one or more inorganic, organic or organometallic insecticides, acaracides, fungicides, nematicides, disinfectants, and herbicides. Examples of the above include dimethylcarbate; calcium and lead arsenates; elementary sulfur and inorganic sulfur compounds, e.g. calcium polysulfide and sodium thiosulfate; copper, zinc and other metal inorganics, such as copper carbonate, copper oxychloride, copper sulfate, and copper zinc sulfate; alcohols including unsaturated and cyclic alcohols; aldehydes such as formaldehyde and metaldehyde; aliphatic amines, e.g. di-n-octylamine, benerin, nitralin, and trifluralin; mixed esters of carbonic acid; carbamic acid and its derivatives, e.g. aryl esters of N-methylcarbamic acid, and alkyl esters of N-aryl-carbamic acid; thio- and dithio-carbamic acid derivatives; salicylanilide; heterocyclic compounds, e.g. copper quinolate; aliphatic mercaptans, e.g. methyl mercaptan; organic sulfides and thioacetals; organic nitro compounds, e.g. chloropicrin; trialkyl and triaryl tin compounds; organic copper and zinc compounds, e.g. copper linoleate, copper naphthanate, and copper quinolate; phenols, e.g. dinocap and dinobuton, organo phosphorus compounds, e.g. DDVP, tris (2,4-dichlorophenoxyethyl) phosphite, and chlorpyrifos; thiophosphoric acid derivatives and pyrophosphoric acid derivatives; phosphonic acid derivatives, e.g. Trichlorofon® and Trichloronate®; quinones, e.g. chlorobenzoquinone; aromatic esters of arylsulfonic acids; thiocyanates and isocyanates; urea and thiourea derivatives; phenoxy acid herbicides such as (4-chloro-2-methylphenoxy) acetic acid, 4-(2-methyl-4-chlorophenoxy) butyric acid, 2,4-dichlorophenoxy acetic acid, 4-(2,4-dichlorophenoxy) butyric acid, and 2-methoxy-3,6-dichlorobenzoic acid; and bacterial and botanical compounds, e.g. pyrethrins, *Bacillus thuringiensis* Berliner; nicotine sulfate, juvenile hormones, pheromones, antiallatotropins, phytoalexins, viruses, and genetic control agents.

Other agricultural products can also optionally be present in the aqueous pesticide compositions, such as organic or inorganic fertilizers, e.g. 5-10-5; plant growth hormones, e.g. gibberellins; and the like.

In addition, small quantities of so called "condensed" alkyl naphthalene sulfonates can optionally be added as dispersing agents, e.g., an alkali metal salt of a condensed mono naphthalene sulfonic acid sold under the trade name LOMAR®D and LOMAR®PW by Henkel Corporation, Cedartown, Ga.

The aqueous pesticide compositions of the invention can be applied to plants vines, bushes, and trees using usual ground and air spray equipment.

The invention will be illustrated but not limited by the following examples.

EXAMPLES

Example 1

Seven aqueous solutions containing 0.1% total surfactants were prepared and the surface tensions of the solutions were determined at 25 ° C. using a Lauda Tensiometer TE 1C. The compositions of the surfactants in the aqueous solutions and the surface tensions of the aqueous solutions are set forth in Table 1 below.

TABLE 1

| Surfactant composition, wt. % | | |
|---|---|---|
| Sodium diisopropyl naphthalene sulfonate | 45% $C_8$/55% $C_{10}$ straight chain alkyl polyglycoside (n = 1.7) | Surface Tension, dynes/cm |
| 100 | 0 | 46.3 |
| 90 | 10 | 40.0 |
| 80 | 20 | 34.8 |
| 60 | 40 | 30.5 |
| 40 | 60 | 28.6 |
| 20 | 80 | 27.7 |
| 0 | 100 | 27.1 |

The results set forth in the above Table I show that relatively small quantities of the alkyl polyglycoside result in a substantial decrease in the surface tension of the aqueous surfactant mixtures. These results are given in graph form in FIG. I, where the straight line is the expected surface tension for the surfactant mixtures.

Example 2

Seven 0.1% aqueous solutions were prepared and the surface tensions measured as in Example 1. The results are set forth in Table 2 below.

TABLE 2

| Surfactant composition, wt. % | | |
|---|---|---|
| Sodium sec. butyl naphthalene sulfonate | 45% $C_8$/55% $C_{10}$ straight chain alkyl polyglycoside (n = 1.7) | Surface Tension, dynes/cm |
| 100 | 0 | 42.1 |
| 90 | 10 | 35.1 |
| 80 | 20 | 31.1 |
| 60 | 40 | 29.1 |
| 40 | 60 | 28.3 |
| 20 | 80 | 28.0 |
| 0 | 100 | 27.1 |

Figure 2:
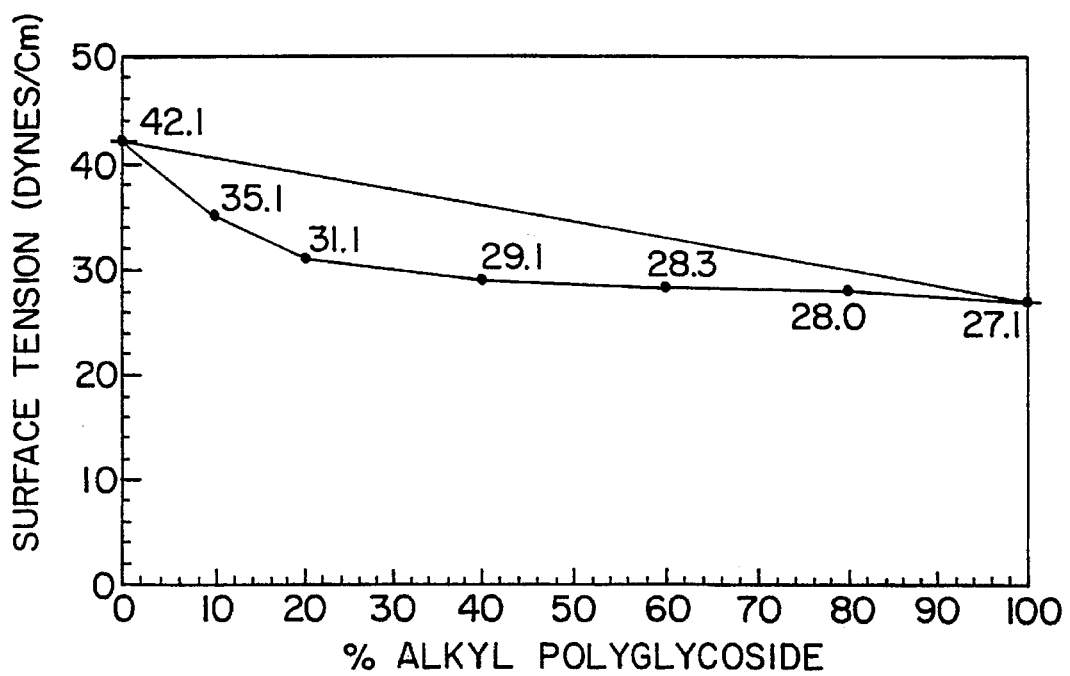

The results set forth in the above Table 2 also show that relatively small quantities of an alkyl polyglycoside result in a substantial decrease in the surface tension of the aqueous surfactant mixtures. These results are given in graph form in FIG. 2, where the straight line is the expected surface tension for the surfactant mixtures.

Example 3

Seven 0.1% aqueous solutions were prepared and the surface tensions measures as in Example 1. The results are set forth in Table 3 below.

TABLE 3

| Surfactant composition, wt. % | | |
|---|---|---|
| Sodium diisopropyl naphthalene sulfonate | 20% $C_9$/40% $C_{10}$/40% $C_{11}$ straight chain alkyl polyglycoside (n = 1.6) | Surface Tension, dynes/cm |
| 100 | 0 | 48.1 |
| 90 | 10 | 35.4 |
| 80 | 20 | 31.4 |
| 60 | 40 | 29.4 |
| 40 | 60 | 28.3 |
| 20 | 80 | 27.5 |
| 0 | 100 | 27.4 |

Figure 3:
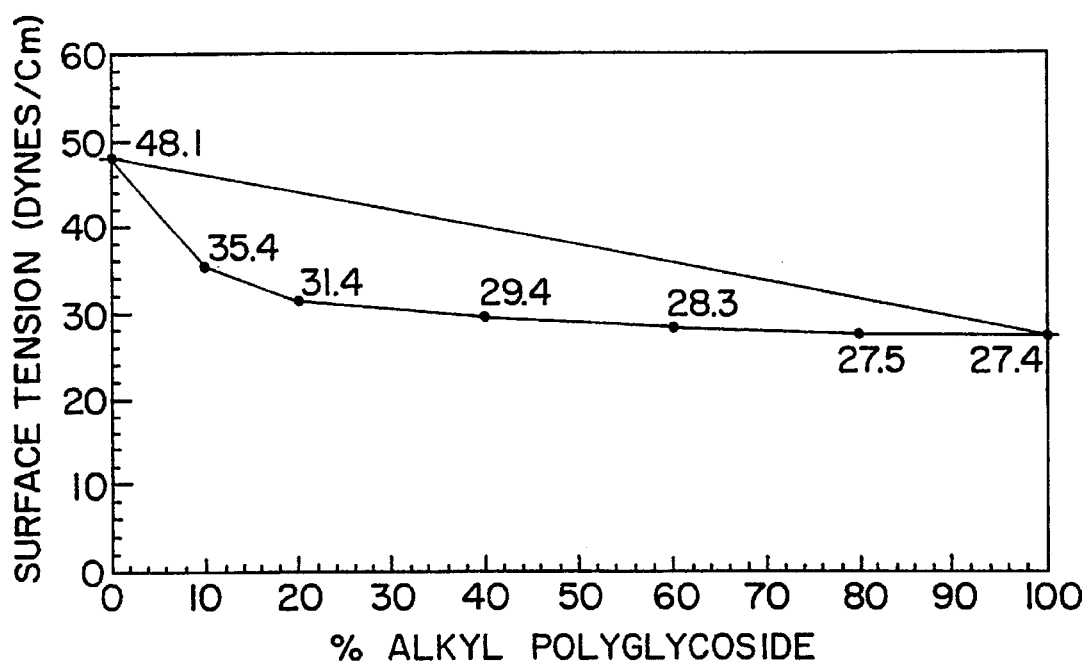

The results set forth in the above Table 3 also show that relatively small quantities of an alkyl polyglycoside result in a substantial decrease in the surface tension of the aqueous surfactant mixtures. These results are given in graph form in FIG. 3, where the straight line is the expected surface tension for the surfactant mixtures.

Example 4

Seven 0.1% aqueous solutions were prepared and the surface tensions measured as in Example 1. The results are set forth in Table 4 below.

TABLE 4

| Surfactant composition, wt. % | | |
|---|---|---|
| Sodium sec. butyl naphthalene sulfonate | 20% $C_9$/40% $C_{10}$/40% $C_{11}$ straight chain alkyl polyglycoside (n = 1.6) | Surface Tension, dynes/cm |
| 100 | 0 | 42.7 |
| 90 | 10 | 32.7 |
| 80 | 20 | 29.7 |
| 60 | 40 | 28.8 |
| 40 | 60 | 28.2 |
| 20 | 80 | 27.8 |
| 0 | 100 | 27.5 |

Figure 4:
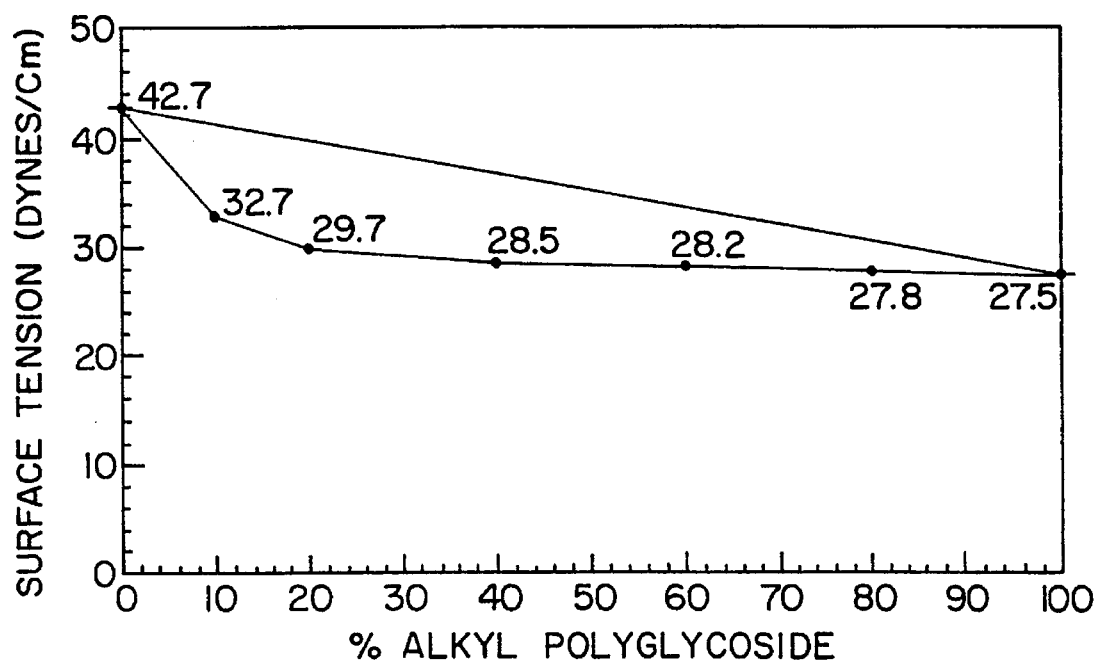

The results set forth in the above Table 4 also show that relatively small quantities of an alkyl polyglycoside result in a substantial decrease in the surface tension of the aqueous surfactant mixtures. These results are given in graph form in FIG. 4, where the straight line is the expected surface tension for the surfactant mixtures.

What is claimed is:

1. A pesticidal surfactant mixture comprising
   A) at least one alkyl naphthalene sulfonate; and
   B) at least one alkyl polyglycoside of the formula $$R^2—O(G)_n \qquad (II)$$

wherein $R^2$ is a $C_{8-22}$ alkyl or alkenyl radical, G is a glycose unit, and n is a number from 1 to 10;
   wherein component B) is present in from about 5 to about 25% by weight based on the total weight of components A) plus B).

2. The surfactant mixture of claim 1 wherein component B) is present in from about 10 to about 20% by weight based on the total weight of components A) plus B).

3. The surfactant mixture of claim 1 wherein in component B) n is from about 1.2 to about 1.8.

4. The surfactant mixture of claim 1 wherein in component B) the at least one alkyl glycoside is at least one alkyl glucoside.

5. The surfactant mixture of claim 1 wherein in component B) $R^2$ is $C_{10-18}$ alkyl group.

6. The surfactant mixture of claim 1 wherein the at least one alkyl naphthalene sulfonate of component A) has the formula

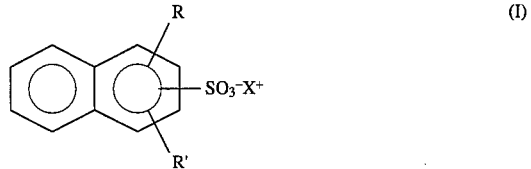

wherein R and R' are independently hydrogen or a $C_{1-30}$ straight or branched chain alkyl or alkenyl group, provided that both R and R' cannot be hydrogen, and x⁻ is hydrogen, an alkali metal, an alkaline earth metal, ammonium, a mono-, di-, or tri- $C_{1-4}$ alkyl ammonium, or a mono-, di-, or tri- $C_{1-4}$ hydroxyalkyl ammonium cation.

7. The surfactant mixture of claim 1 further comprising from about 50 to about 99.9% by weight of water, based on the weight of the aqueous surfactant mixture.

8. The surfactant mixture of claim 6 wherein from about 75 to about 99.9% by weight of water is present therein.

9. An aqueous pesticide composition comprising
   A) at least one alkyl naphthalene sulfonate;
   B) at least one alkyl polyglycoside of the formula $$R^2—O(G)_n \qquad (II)$$

wherein $R^2$ is a $C_{8-22}$ alkyl or alkenyl radical, G is a glycose unit and n is a number from 1 to 10; and
   C) at least one other pesticide;
   wherein component B) is present in from about 5 to about 25% by weight based on the total weight of components A) plus B).

10. The pesticide composition of claim 9 wherein component C) is present in from about 0.001 to about 25% by weight, and the combination of component A) plus component B) is present in from about 0.01 to about 5% by weight, based on the weight of the aqueous pesticide composition.

11. The pesticide composition of claim 9 wherein component B) is present in from about 10 to about 20% by weight based on the total weight of components A) plus B).

12. The pesticide composition of claim 9 wherein in component B) n is from about 1.2 to about 1.8.

13. The pesticide composition of claim 9 wherein in component B) the at least one alkyl glycoside is at least one alkyl glucoside.

14. The pesticide composition of claim 9 wherein in component B) $R^2$ is a $C_{10-18}$ alkyl group.

15. The pesticide; composition of claim 9 wherein the at least one alkyl naphthalene sulfonate of component A) has the formula

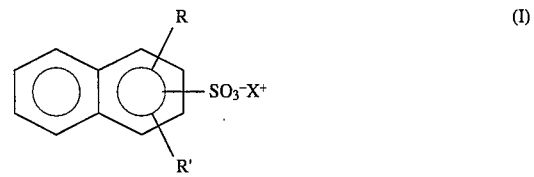

wherein R and R' are independently hydrogen or a $C_{1-30}$ straight or branched chain alkyl or alkenyl group, provided that both R and R' cannot be hydrogen, and $x^-$ is hydrogen, an alkali metal, an alkaline earth metal, ammonium, a mono-, di-, or tri- $C_{1-4}$ alkyl ammonium, or a mono-, di-, or tri- $C_{1-4}$ hydroxyalkyl ammonium cation.

16. The pesticide composition of claim 10 wherein the at least alkyl naphthalene sulfonate of component A) has the formula

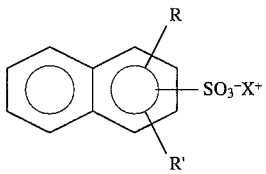

(I)

wherein R and R' are independently hydrogen or a $C_{1-30}$ straight or branched chain alkyl or alkenyl group, provided that both R and R' cannot be hydrogen, and $x^-$ is hydrogen, an alkali metal, an alkaline earth metal, ammonium, a mono-, di-, or tri- $C_{1-4}$ alkyl ammonium, or a mono-, di-, or tri- $C_{1-4}$ hydroxyalkyl ammonium cation; and in component B) n is from about 1.2 to about 1.8, $R^2$ is a $C_{10-18}$ alkyl group, and G is a glucoside group.

17. The pesticide composition of claim 9 wherein the composition also contains at least once other agricultural material therein selected from the group consisting of organic fertilizers, inorganic fertilizers, plant growth hormones, and condensed alkyl naphthalene sulfonates.

18. The pesticide composition of claim 17 wherein the at least one other agricultural material is a fertilizer.

19. The pesticide composition of claim 18 wherein said fertilizer is a mixture of inorganic salts.

20. The pesticide composition of claim 18 wherein component C) is at least one of an acaracide, a fungicide, an insecticide, a nematicide, a herbicide, and a disinfectant.

* * * * *